United States Patent
Hsieh et al.

(10) Patent No.: US 7,756,315 B2
(45) Date of Patent: Jul. 13, 2010

(54) METHOD AND APPARATUS FOR FIELD-OF-VIEW EXPANSION OF VOLUMETRIC CT IMAGING

(75) Inventors: Jiang Hsieh, Brookfield, WI (US); Albert Henry Roger Lonn, Beaconsfield (GB); Mark Lynn Nyka, Sussex, WI (US)

(73) Assignee: General Electric Company, Schenectady, NY (US)

( * ) Notice: Subject to any disclaimer, the term of this patent is extended or adjusted under 35 U.S.C. 154(b) by 961 days.

(21) Appl. No.: 11/286,919

(22) Filed: Nov. 23, 2005

(65) Prior Publication Data

US 2007/0116344 A1    May 24, 2007

(51) Int. Cl.
  *G06K 9/00* (2006.01)
  *A61B 6/00* (2006.01)
(52) U.S. Cl. .......................................... 382/131; 378/4
(58) Field of Classification Search ................. 382/128, 382/131–133; 378/4, 15, 19, 207, 901; 250/363.04
See application file for complete search history.

(56) References Cited

U.S. PATENT DOCUMENTS

| | | | | |
|---|---|---|---|---|
| 4,550,371 A | * | 10/1985 | Glover et al. ................... | 378/4 |
| 5,043,890 A | * | 8/1991 | King ........................ | 382/279 |
| 6,307,909 B1 | * | 10/2001 | Flohr et al. ..................... | 378/4 |
| 6,810,102 B2 | | 10/2004 | Hsieh et al. | |
| 6,856,666 B2 | * | 2/2005 | Lonn et al. ..................... | 378/8 |
| 6,944,260 B2 | | 9/2005 | Hsieh et al. | |
| 7,050,528 B2 | * | 5/2006 | Chen ............................. | 378/4 |
| 7,254,259 B2 | * | 8/2007 | Hsieh et al. .................. | 382/131 |
| 2004/0073584 A1 | | 4/2004 | Hsieh et al. | |
| 2005/0161606 A1 | | 7/2005 | Balan et al. | |

OTHER PUBLICATIONS

Hsieh et al, "A novel reconstruction algorithm to extend the CT scan field-of-view" Medical Physics, vol. 31, No. 9, Sep. 2004.*
J. Hsieh, E. Chao, J. Thibault, B. Grekowicz, A. Horst, S. McOlash, and T. J. Myers, "A novel reconstruction algorithm to extend the CT scan field-of-view", 2004 American Association of Physicists in Medicine [DOI: 10.1118/1/1776673], Med. Phys. 31 (9), Sep. 2004, pp. 2385-2391.

* cited by examiner

*Primary Examiner*—Vu Le
*Assistant Examiner*—Andrae S Allison
(74) *Attorney, Agent, or Firm*—Dean Small; Small Patent Law Group (57) ABSTRACT

A method for expanding a field-of-view of a volumetric computed tomography scan comprises identifying truncated views having projection truncation and non-truncated views without projection truncation based on an average value of one or more edge channels. An estimated missing projection is calculated for each of the truncated views based on at least one neighboring non-truncated view. A projection profile is calculated for each of the truncated views based on the estimated missing projection, and the projection profile provides at least one of attenuation data and projection data for an area outside a field-of-view.

20 Claims, 6 Drawing Sheets

METHOD AND APPARATUS FOR FIELD-OF-VIEW EXPANSION OF VOLUMETRIC CT IMAGING

BACKGROUND OF THE INVENTION

This invention relates generally to processing image data acquired by a system having volumetric computed tomography (VCT) capability, and more particularly, to expanding the field-of-view of a CT scanner.

The current hardware of the volumetric CT (VCT) scanner has a reconstruction field-of-view (FOV) that is limited to 50 cm. Although sufficient for many clinical applications, it is desirable to expand the FOV to image objects currently outside the FOV. This is particularly advantageous for applications such as oncology and multi-modality imaging, such as CT combined with at least one of positron emission tomography (PET) and single photon emission computed tomography (SPECT) capability. For example, in multi-modality imaging using a CT/PET system, the FOV of the PET system may be larger than the FOV of the CT system. In some applications, it is desirable to have a consistent FOV between the CT and the other (PET or SPECT) imaging system.

By way of example, for oncology applications, a larger FOV may be desirable as the limbs of the patient are often positioned outside the FOV of the CT detector for better tumor positioning during radiation treatment planning. The current VCT reconstruction algorithm ignores the truncated projections (data outside the FOV) and produces images with severe artifacts which may negatively affect an accurate estimation of the attenuation path for treatment planning.

Combined PET/CT and SPECT/CT scanners obtain inherently registered PET (or SPECT) and CT images, which are used to produce a fused image. For example, the PET emission data is corrected for the attenuation of the 511 keV photons (or positrons) using an attenuation map derived from the CT image. The VCT images have a smaller FOV (50 cm) than the PET scanner (70 cm), resulting in missing attenuation data from structures outside 50 cm. CT artifacts resulting from truncated data propagate into the PET image and result in corruption. Therefore, expanding the VCT FOV to match the PET FOV is highly desirable.

Missing projections have been compensated for in various ways. Many of the corrections rely on the consistency condition of the measured projection data to estimate the missing projection. For example, for a parallel beam geometry, the total amount of attenuation of a single projection does not change over different angles. When the cone angle is small, such as approximately 1 degree for a 16 slice CT scanner, this assumption is approximately valid.

However, the consistency condition does not work well in cone beam configuration where the cone angle may be approximately 4 degrees or larger. The divergent nature of the cone beam can no longer be ignored. For a 16 slice CT scanner, a plot of total attenuation as a function of a view results in a relatively straight line. For VCT, however, the plot is an odd shaped curve and can no longer be used to determine where truncation takes place or what area of an object is outside the FOV. For example, as the scanner rotates around the patient, outer rows with axial angles of more than two degrees measure attenuation through a changing section of the patient. Thus the plot of total attenuation per projection around the patient is modulated by the axial variation in the patient, making it difficult to detect variations which may be caused by truncation of the transaxial FOV.

Therefore, a need exists for increasing the FOV coverage of a CT scanner. Certain embodiments of the present invention are intended to meet these needs and other objectives that will become apparent from the description and drawings set forth below.

BRIEF DESCRIPTION OF THE INVENTION

In one embodiment, a method for expanding a field-of-view of a volumetric computed tomography scan comprises identifying truncated views having projection truncation and non-truncated views without projection truncation based on an average value of one or more edge channels. An estimated missing projection is calculated for each of the truncated views based on at least one neighboring non-truncated view. A projection profile is calculated for each of the truncated views based on the estimated missing projection. The projection profile provides at least one of attenuation data and projection data for an area outside a field-of-view.

In another embodiment, a method for expanding a field-of-view of a computed tomography scanner comprises identifying truncated views having projection truncation and non-truncated views without projection truncation based on an average value of one or more edge channels. A total estimated missing projection is calculated based on a total attenuation curve representative of measured total attenuation for each of the truncated and non-truncated views. A projection profile is calculated for each of the truncated views based on at least one of the total estimated missing projection and a projection profile representative of at least one non-truncated view being closest to each of the truncated views. The projection profile provides at least one of attenuation data and projection data for an area outside a field-of-view.

In another embodiment, a system for expanding a field-of-view comprises a computer for receiving computed tomography image data representative of multiple views. The computer is configured to identify truncated views having projection truncation and non-truncated views without projection truncation based on an average value of one or more edge channels. The computer calculates an estimated missing projection for each of the truncated views based on at least one neighboring non-truncated view. The computer calculates a projection profile for each of the truncated views based on the estimated missing projection, the projection profile providing at least one of attenuation data and projection data for an area outside a field-of-view.

The foregoing summary, as well as the following detailed description of certain embodiments of the present invention, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF THE INVENTION

Figure 1:
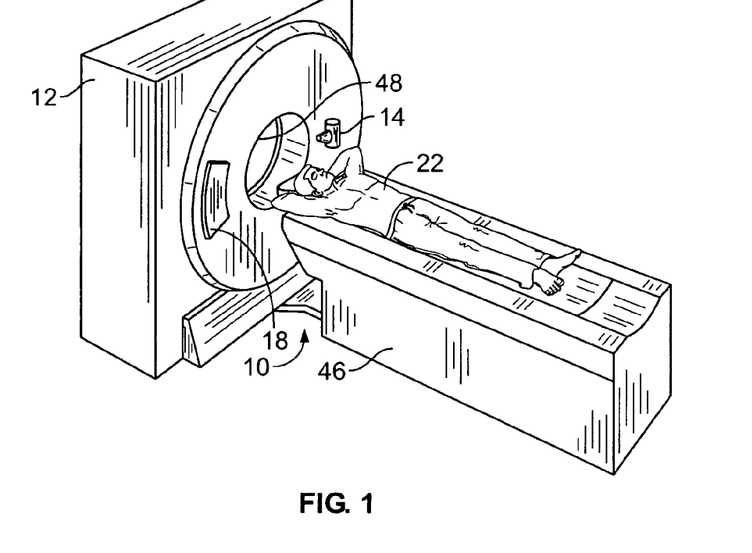
FIG. 1 is a pictorial view of a CT imaging system.
Figure 2:
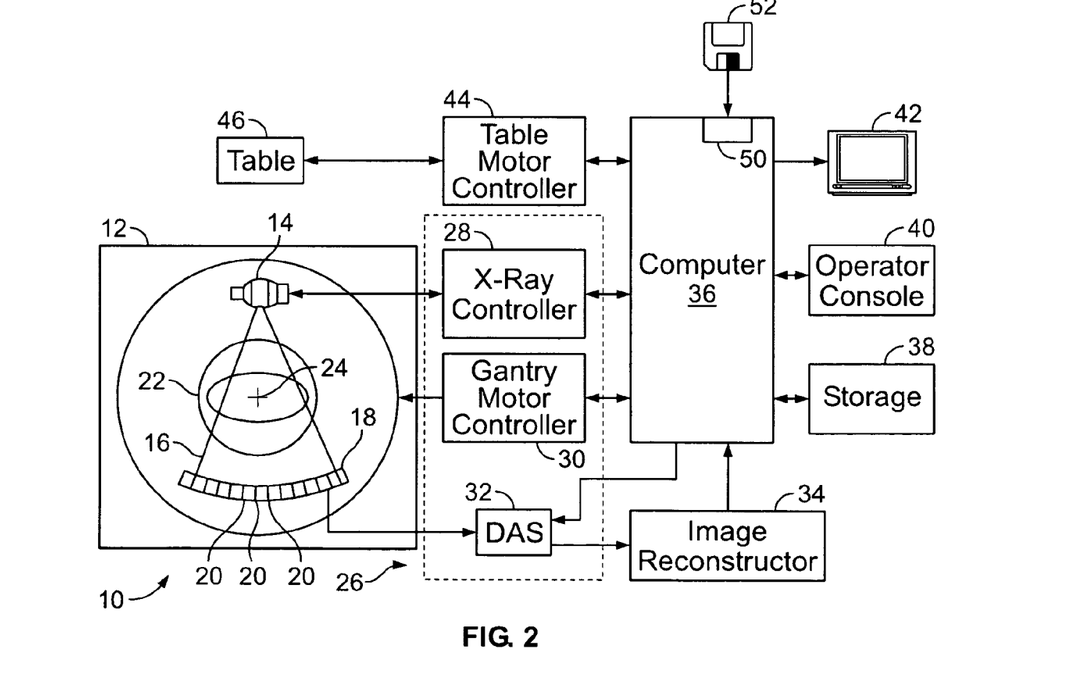
FIG. 2 is a block schematic diagram of the system illustrated in FIG. 1.

FIGS. 1 and 2 illustrate a multi-modality imaging system 10 which include a first modality unit and a second modality unit (not shown). The two modality units enable the imaging system 10 to scan an object in a first modality using the first modality unit and to scan the object in a second modality using the second modality unit. Imaging system 10 allows for multiple scans in different modalities to facilitate an increased diagnostic capability over single modality systems. For example, multi-modal imaging system 10 may be a Computed Tomography/Positron Emission Tomography (CT/PET) imaging system having a gantry 12 representative of a "third generation" CT imaging system in combination with PET circuitry (not shown). The PET circuitry includes a plurality of PET detectors and a processor (not shown) which, among other things, includes coincidence detection circuitry. The PET detectors and detector array 18 both detect radiation and are both referred to herein as radiation detectors. Alternatively, the imaging system 10 may be a combination CT and single photon emission computed tomography (SPECT) imaging system having the gantry 12 in combination with SPECT circuitry, such as one or more detectors to detect gamma radiation. It should be understood that a single detector array may acquire CT and PET or SPECT radiation data simultaneously.

Gantry 12 includes the first modality unit which has an x-ray source 14 that projects a beam of x-rays 16 toward a detector array 18 on the opposite side of the gantry 12. Detector array 18 is formed by a plurality of detector rows (not shown) including a plurality of detector elements 20 which together sense the projected x-rays that pass through an object, such as a patient 22. The detector elements 20 may also sense gamma rays and/or positrons. Each detector element 20 produces an electrical signal that represents the intensity of an impinging x-ray beam and hence allows estimation of the attenuation of the beam as it passes through object or patient 22.

During a scan to acquire x-ray projection data, gantry 12 and the components mounted thereon rotate about a center of rotation 24. FIG. 2 illustrates a single row of detector elements 20 (i.e., a detector row), however, a multislice detector array 18 includes a plurality of parallel detector rows of detector elements 20 such that projection data corresponding to a plurality of slices may be acquired simultaneously during a scan. Optionally, a "helical" scan may be performed wherein the patient is moved while the data for the prescribed number of slices is acquired. Such a system generates a single helix from a fan beam helical scan. The helix mapped out by the fan beam yields projection data from which images in each prescribed slice may be reconstructed. A group of x-ray attenuation measurements, i.e., projection data, from the detector array 18 at one gantry angle is referred to as a "view". A "scan" of the object comprises a set of views made at different gantry angles, or view angles, during one revolution of the x-ray source 14 and detector array 18.

Rotation of the gantry 12 and operation of the x-ray source 14 are governed by a control mechanism 26 of imaging system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has input devices such as a keyboard, mouse, touchscreen, microphone for voice commands, and the like. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position the patient 22 in the gantry 12. Particularly, the table 46 moves portions of the patient 22 through the gantry opening 48.

In one embodiment, the computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital formats and systems. In another embodiment, computer 36 executes instructions stored in firmware (not shown). The computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Alternatively, the computer 36 may be a stand-alone configuration, typically used for processing, displaying and reviewing image data stored in a storage device, such as storage device 38, or an optical or compact disc, for example.

Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
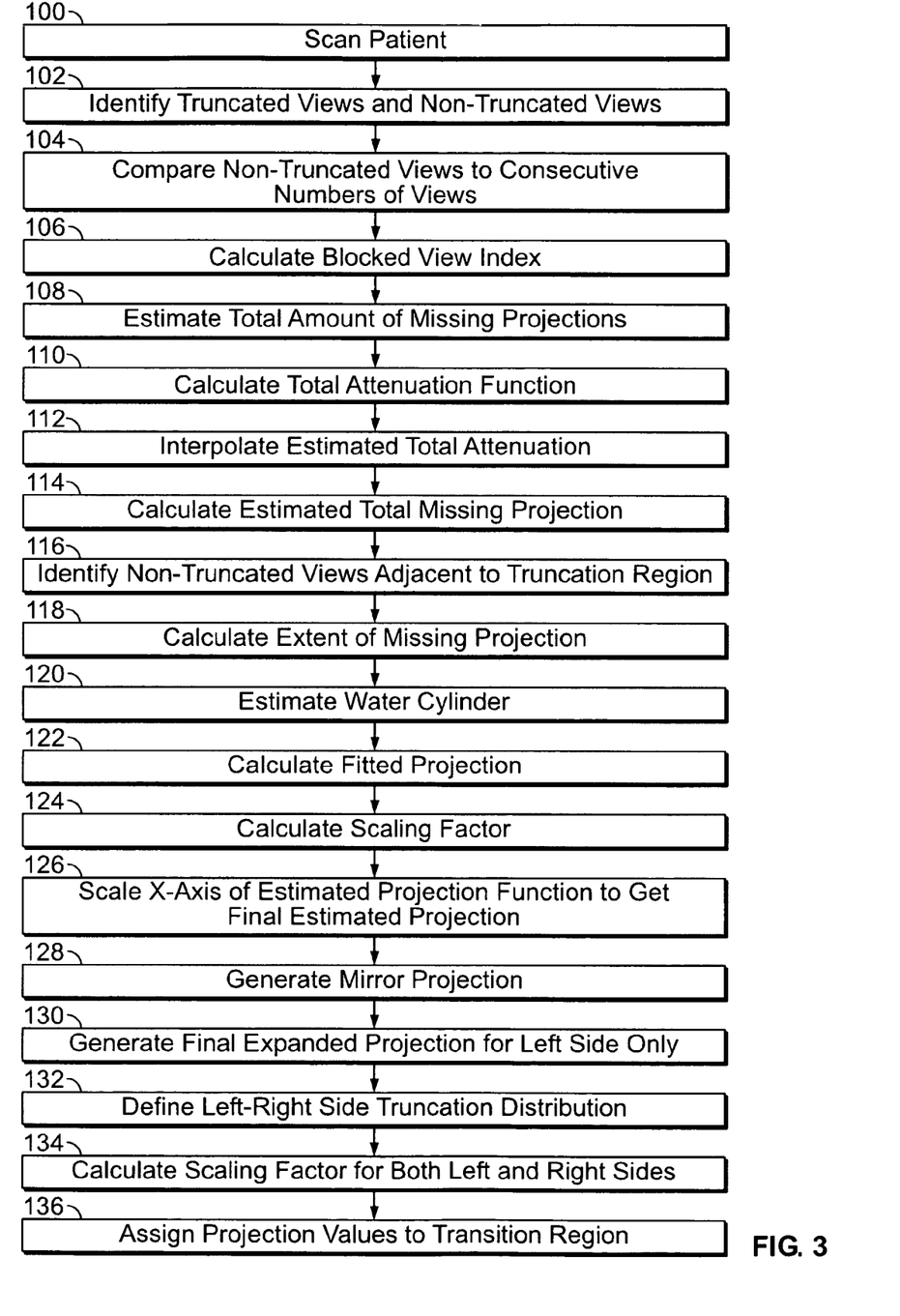
FIG. 3 illustrates a method for expanding the FOV of a VCT scan in accordance with an embodiment of the present invention.

FIG. 3 illustrates a method for expanding the FOV of a VCT scan in accordance with an embodiment of the present invention. In step 100, a patient is scanned by the imaging system 10. Alternatively, previously acquired scan data is accessed, which may be stored in storage device 38. A projection profile for each view is generated by the computer 36 based on the projection samples. Under some scanning conditions as previously discussed, portions of the patient 22 may extend beyond the FOV of the CT detector array 18, which may lead to image artifacts and an incomplete representation of the imaged object.

In step 102, the computer 36 identifies truncated views and non-truncated views. Edge channel readings are relied on as it is not possible to use the total attenuation of a projection as the measurement of projection truncation. For example, when no object is present in the beam path, the projection reading after the calibration should be substantially zero. If, however, the scanned object is continuous and extends beyond the FOV, a truncated projection is defined when the x-ray beam path corresponding to the edge channels is blocked by the object. Therefore, the corresponding edge projection readings are significantly higher than zero when going through a patient (truncated projection), and will be zero if going through air (non-truncated projection). To avoid noise impact, blocked view candidates $B_L(k)$ and $B_R(k)$ are compared to a threshold and identified using Equations 1 and 2, respectively:

$$B_L(k, j) = \begin{cases} 1, & \text{if } \frac{1}{n}\sum_{i=0}^{n-1} p_k(i, j) \geq t \\ 0, & \text{otherwise} \end{cases} \quad \text{Equation 1}$$

$$B_R(k, j) = \begin{cases} 1, & \text{if } \frac{1}{n}\sum_{i=N-n}^{N-1} p_k(i, j) \geq t \\ 0, & \text{otherwise} \end{cases} \quad \text{Equation 2}$$

wherein $p_k(i, j)$ represents the row-to-row fan-to-parallel rebinned projection sample of the $i^{th}$ channel, $j^{th}$ row, and $k^{th}$ view. (It should be noted that a similar approach may be applied to the original cone beam projection to identify truncated views.) N is the number of detector elements 20 in a row, and n is the number of samples to average. Subscripts "L" and "R" stand for left and right sides of the projection, respectively. Therefore, if the average of X channels is larger than a threshold, the channel is declared to be a truncation candidate.

Figure 4:
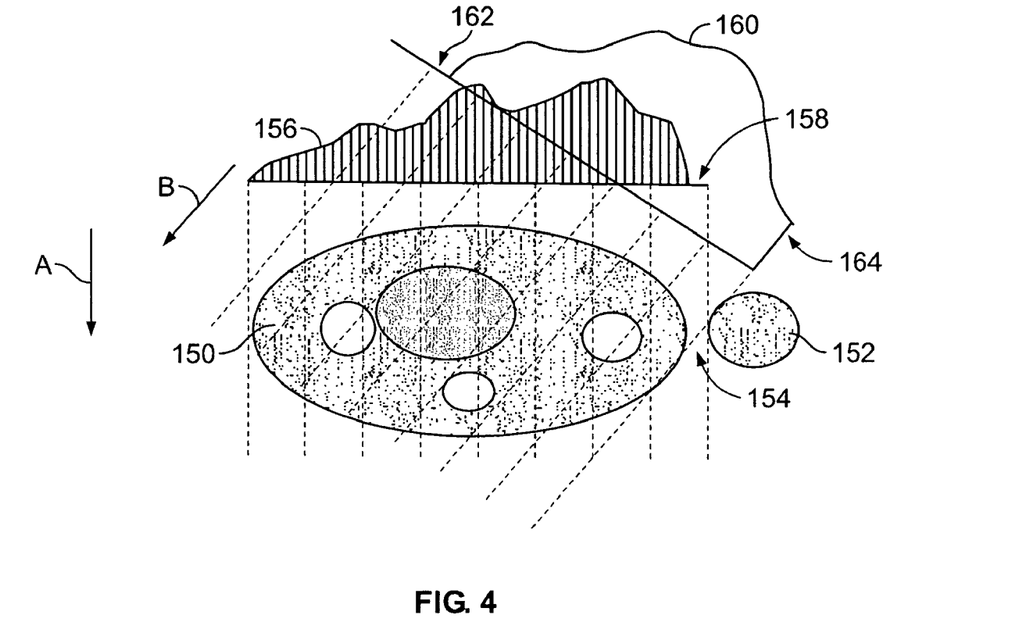
FIG. 4 illustrates the detection of projection truncation in accordance with an embodiment of the present invention.

FIG. 4 illustrates the detection of projection truncation in accordance with an embodiment of the present invention. Structure 150 represents a main body, such as an abdomen of a subject, while structure 152 represents an arm or other structure separated from the structure 150 by an air gap 154. The structure 152 may be positioned outside the CT scan FOV for one or more scan angles, such as between 50 cm and 70 cm.

For a first view, the x-ray source 14 directs x-rays in the direction of arrow A which are detected by the detector array 18. The resulting projection samples are represented by projection profile 156. A portion 158 reflects where the edge projection samples are zero, as the x-rays pass through the air gap 154 and are not attenuated by either structure 150 or 152. The gantry 12 rotates the x-ray source 14 and detector array 18. For a second view, the x-ray source 14 directs x-rays in the direction of arrow B and the resulting projection samples are represented by projection profile 160. Portion 162 reflects where the edge projection samples are zero, as the x-rays pass through air beyond the structure 150. On opposite end 164 of the projection profile 160, however, the x-rays are attenuated by one or both of the structures 150 and 152, resulting in non-zero edge projection samples. It should be understood that many other views may be acquired between the first and second views. Under such conditions, if the edge projection samples in the portion 158 of the projection profile 156 remain zero, the first projection may be wrongly classified as a non-truncated projection based on Equations 1 and 2, as structure 152 exists beyond the portion 158.

In step 104 (FIG. 3), the computer 36 compares views classified as non-truncated projections to a predetermined consecutive number of views. Step 104 prevents the wrong classification, such as with the first projection above. If during a search over the predetermined consecutive number of views, no other view is truncated, the view remains classified as non-truncated. For example, when a small space such as the air gap 154 exists between the structures 150 and 152, only a few views that are in alignment with the air gap 154 have zero edge channel readings. When the gantry 12 is rotated slightly, the air gap 154 is no longer present from the viewpoint of the current projection, and the edge channels are non-zeroes, as shown by the second view and projection profile 160. Therefore, the non-truncated view which was wrongly classified is reassigned as a truncated view if a number of consecutive views having zero edge channel readings are less than a predetermined threshold in Equation 3:

$$B'_L(k, j) = \begin{cases} 0, & \text{if } B_L(k, j) = 0 \quad \forall k_s \leq k \leq k_e, \text{ and } k_e - k_s \geq m_t \\ 1, & \text{otherwise} \end{cases} \quad \text{Equ. 3}$$

$$B'_R(k, j) = \begin{cases} 0, & \text{if } B_L(k, j) = 0 \quad \forall k_s \leq k \leq k_e, \text{ and } k_e - k_s \geq m_t \\ 1, & \text{otherwise} \end{cases} \quad \text{Equ. 3}$$

wherein $m_t$ is a parameter specifying the minimum number of consecutive non-truncated projections to ensure that a non-truncated projection is correctly classified as non-truncated. By way of example only, the parameter $m_t$ may be 20 consecutive non-truncated projections.

In step 106, the computer 36 calculates a blocked view index using Equation 4, which is the union of the left and right blockage calculated in Equation 3:

$$B'(k, j) = B'_L(k, j) \cup B'_R(k, j) \quad \text{Equation 4}$$

The blocked view index ensures that a view is classified as non-truncated only if both conditions (i.e. left and right sides) are satisfied.

In step 108, the computer 36 estimates the total amount of missing projections for each truncated view identified by Equation 4. Although conservation of total attenuation does not hold for rebinned projections, the total attenuation curve is still a continuous function. Therefore, adjacent non-truncated views may be used to estimate the missing projection of a truncated view.

Figure 5:
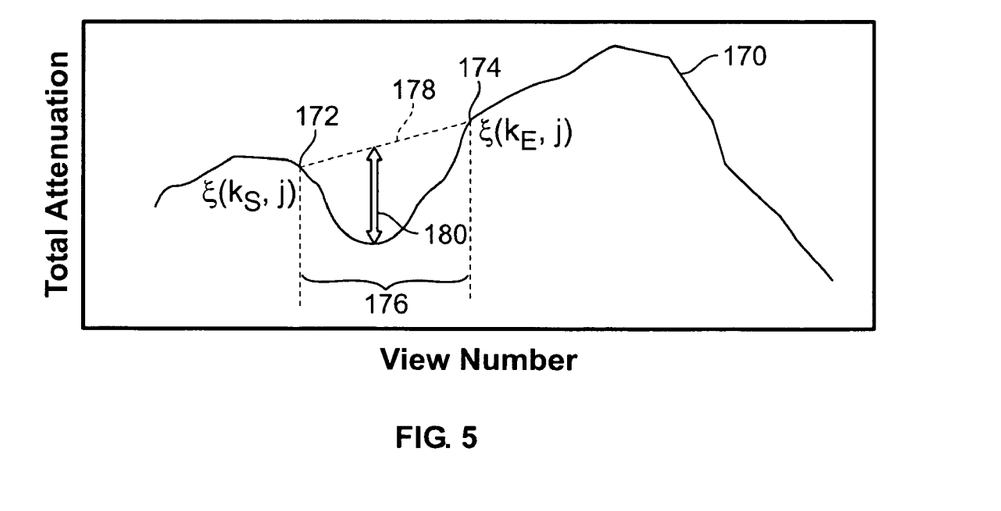
FIG. 5 illustrates a measured total attenuation representative of truncated views and adjacent non-truncated views in accordance with an embodiment of the present invention.

FIG. 5 illustrates a measured total attenuation 170 representative of truncated views and adjacent non-truncated views in accordance with an embodiment of the present invention. The measured total attenuation 170 is illustrated over consecutively acquired views and is not a flat curve due to the size of the cone angle. Based on Equations 1-4, the non-truncated channels may be identified.

A first non-truncated view 172 and a second non-truncated view 174 are illustrated adjacent to a truncation view region 176. In step 110, the computer 36 calculates a total attenuation function, ξ(k, j), for view k and row j, with Equation 5:

$$\xi(k, j) = \sum_i p_k(i, j) \qquad \text{Equation 5}$$

In step 112, the computer 36 interpolates an estimated total attenuation without truncation 178, ξ'(k, j) from the two untruncated values ξ(k$_S$, j) and ξ(k$_E$, j) calculated with Equation 5 which correspond to the first and second non-truncated views 172 and 174. For example, linear interpolation may be used to determine a first approximation of the value of the estimated total attenuation without truncation 178 ξ'(k, j) with Equation 6:

$$\xi'(k, j) = \frac{k_E - k}{k_E - k_S}\xi(k_S, j) + \frac{k - k_S}{k_E - k_S}\xi(k_E, j) \qquad \text{Equation 6}$$

For simplicity, Equation 6 may assume that as the distance is small between the first and second non-truncated views 172 and 174, the amount of attenuation change is small. Therefore, linear interpolation may be used to provide the first order of approximation. In other words, if there were no truncation projections, the truncation view region 176 would resemble the estimated total attenuation without truncation 178.

In step 114, the computer 36 calculates estimated total missing projection 180, D(k, j), for view k and row j, with Equation 7 as the difference between the estimated total attenuation without truncation 178 and the measured total attenuation 170:

$$D(k, j) = \xi'(k, j) - \xi(k, j) \qquad \text{Equation 7}$$

The estimated total missing projection 180 is now known, however, the distribution of the estimated total missing projection 180 over the extended channels is not known.

Figure 6:
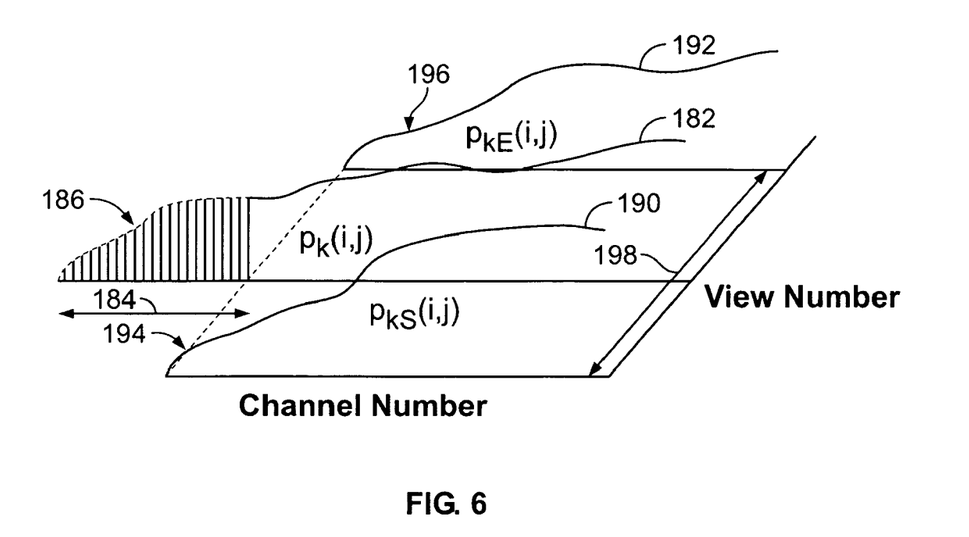
FIG. 6 illustrates an estimation of projection distribution based on adjacent measured projections in accordance with an embodiment of the present invention.

FIG. 6 illustrates an estimation of projection distribution based on adjacent measured projections in accordance with an embodiment of the present invention. The X-axis represents detector channels. Each projection is plotted as a function of detector channel to form a projection profile. In step 116, the computer 36 identifies non-truncated views adjacent to a truncation region. First non-truncated projection profile 190 corresponds to a last non-truncated view and second non-truncated projection profile 192 corresponds to a first non-truncated view after passing truncation region 198. A truncated projection profile 182 corresponds to a truncated view. It should be understood that additional truncated projection profiles within the truncation region 198 may exist but are not illustrated.

The first and second non-truncated projection profiles 190 and 192 correspond to the nearest adjacent non-truncated views, such as the first and second non-truncated views 172 and 174 (FIG. 5), respectively. It may be assumed that a profile of estimated missing projection 186 of the truncated projection profile 182 is closely related to the projection distribution of the first and second non-truncated projection profiles 190 and 192 on both sides of the truncation region 198. Therefore, the profile of the estimated missing projection 186 ($p_k$(i, j)), although it may be shifted, has a shape similar to, and somewhere in between, first adjacent projection profile 194 ($p_{kS}$(i, j)) and second adjacent projection profile 196 ($p_{kE}$(i, j)), where k$_s$ and k$_E$ are the two views adjacent to the truncation region 198.

For simplicity, the case in which only one side of the projection is truncated will be discussed. That is, the projection is truncated on the left or right side, but not both. The case having both is discussed further below. With one side of the projection truncated, the estimated total missing projection 180, D(k, j), (Equation 7) should equal the sum of the estimated projection samples, $p_k$(i, j), as shown by the vertically shaded region under the profile of the estimated missing projection 186 in FIG. 6. As the profile of the estimated missing projection 186 is assumed to have a shape similar to the first and second non-truncated projection profiles 190 and 192 ($p_{kS}$(i, j) and $p_{kE}$(i, j)), in step 118, the computer 36 estimates an extent 184 of the truncation using both the first and second non-truncated projection profiles 190 and 192. The extent 184 identifies the number of non-zero channels in the truncated projection. To find the extent 184, two accumulative projection functions are first calculated with Equations 8 and 9:

$$\eta_{kS}(m, j) = \sum_{i=0}^{m} p_{kS}(i, j) \qquad \text{Equation 8}$$

$$\eta_{kE}(m, j) = \sum_{i=0}^{m} p_{kE}(i, j) \qquad \text{Equation 9}$$

The location, $m_S$ and $m_E$, is then calculated such that $\eta_{kS}(m_S, j) = D(k, j)$ and $\eta_{kS}(m_S, j) = D(k, j)$. The extent 184 of the truncation, $m_k$, along the channel direction for view k is the linear combination of the two values which may be found using Equation 10:

$$m_k = \frac{k - k_S}{k_E - k_S}m_S + \frac{k_E - k}{k_E - k_S}m_E \qquad \text{Equation 10}$$

The extent 184 of the truncation and the magnitude of truncation at the edge channel (size of projection or channel reading at the last non-truncated channel) are now known. Based on the two parameters, the extent 184 and the magnitude, in step 120, the computer 36 calculates a location and size of a water cylindrical object that can best fits the missing projection. The water cylinder may be used to approximate human soft tissue.

Figure 7:
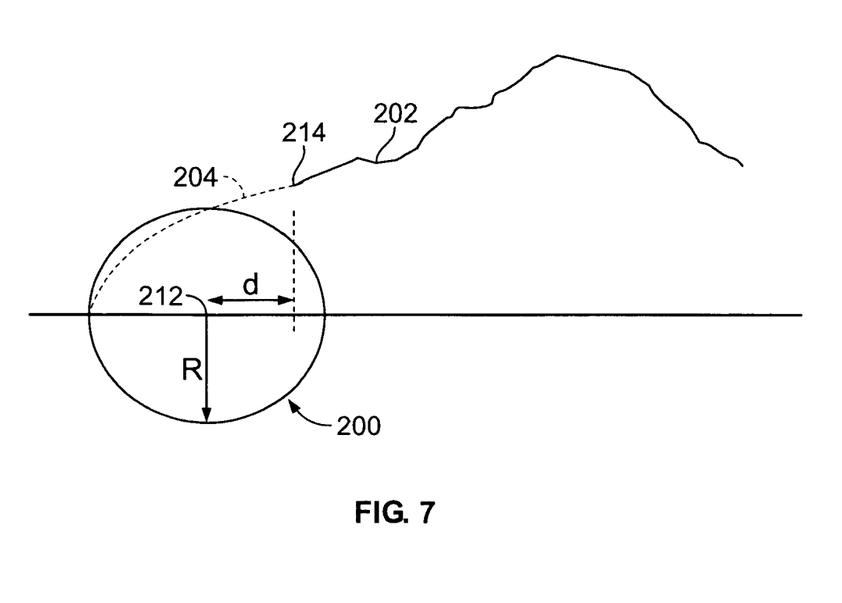
FIG. 7 illustrates a water cylinder projection fitting of a water cylindrical object in accordance with an embodiment of the present invention.

FIG. 7 illustrates a water cylinder projection fitting of a water cylindrical object 200 in accordance with an embodiment of the present invention. Measured projection 202 is a subset of the measured total attenuation 170 (FIG. 5). In Equation 11, the location and the size of the water cylindrical object 200 that best fits the missing projection are calculated:

$$\begin{cases} R = \frac{1}{2}m_k + \frac{1}{8\mu_w^2}\left[\frac{1}{n}\sum_{i=0}^{n-1}p_k(i, j)\right]^2 \\ d = m_k - R \end{cases} \qquad \text{Equation 11}$$

wherein d is the distance from a cylinder disc center 212 to the left of truncated projection edge 214, and R is the radius of the water cylindrical object 200. Equation 11 specifically calculates for the left truncation, although it should be understood that the right side truncation may be treated in a similar manner.

In step 122, the computer 36 calculates fitted projection 204 ($p'_k(i, j)$) based on d and R using Equation 12:

$$p'_k(i, j) = 2\mu_w \sqrt{R^2 - (i+d)^2}, \quad m_k \leq i < 0 \qquad \text{Equation 12}$$

The fitted projection 204 is a calculated set of missing projections or candidates of missing projections. Because the fitted projection 204 ($p'_k(i, j)$) is based on a water cylinder, some errors may be present. To further compensate for either underestimation or overestimation, the total attenuation of the fitted projection 204 is compared against the previously estimated total missing projection 180 (FIG. 5), deriving a scaling factor to adjust for estimation error. In step 124, the computer 36 calculates the scaling factor, g, using Equation 13:

$$g = \frac{D(k, j)}{\sum_{i=m_k}^{-1} p'_k(i, j)} \qquad \text{Equation 13}$$

Given the potential error in the estimated total missing projection 180 (D(k,j)) and the impact of noise, a function of g, f(g), is used so that only a portion of the adjustment g is actually carried out. By way of example only, f(g) may be made equal to $\sqrt{g}$.

Figure 8:
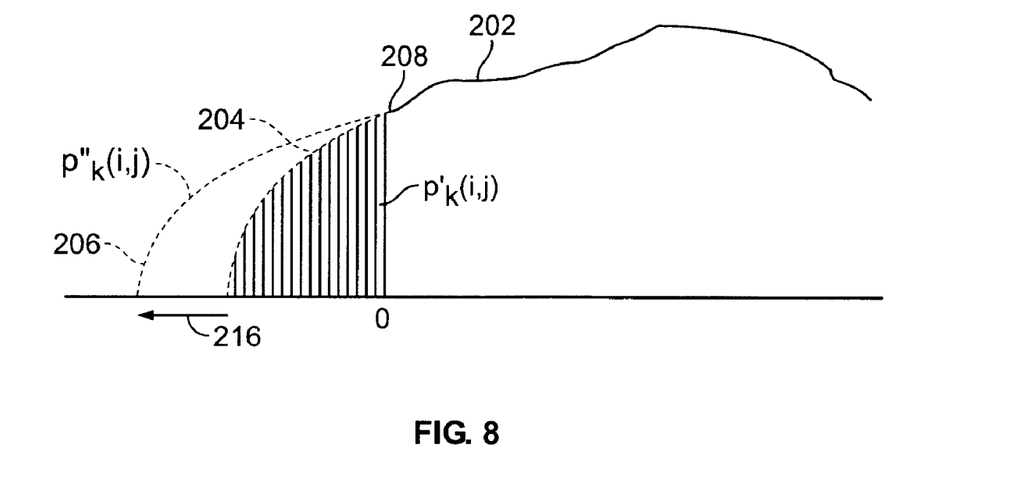
FIG. 8 illustrates a scaling of the fitted projection of FIG. 7 in accordance with an embodiment of the present invention.

FIG. 8 illustrates a scaling of the fitted projection 204 of FIG. 7 in accordance with an embodiment of the present invention. 0 indicates a junction between truncated and non-truncated channels, or a truncation boundary 208. In other words, the truncation boundary 208 is between a truncated projection and a measured projection. In step 126, the computer 36 scales the horizontal axis of the estimated projection function, $p'_k(i, j)$, by the f(g) to arrive at a final estimated projection 206 ($p''_k(i, j)$) with Equation 14:

$$p''_k(i, j) = p'_k(g \cdot i, j) \qquad \text{Equation 14}$$

Note that when the scaling factor g>1, the estimated projection ($p'_k(i, j)$) underestimates the true projection. By stretching the channel axis by a factor of g, the total attenuation of $p'_k(i, j)$ is increased by a factor of g as illustrated by arrow 216. Conversely, if g<1, the estimated projection ($p'_k(i, j)$) overestimates the true projection and the channel axis is compressed by a factor of g to be within the shaded region (not shown).

Because of the frequency characteristics of the ramp filter used when reconstructing the image, any small perturbation in the projection may cause streaking or ring artifacts. For example, if the computing operation is a derivative operation, any discontinuities in slope will generate large errors which will propagate into the image as streaks, arcs or rings. Therefore, the differentiability of the projection at the truncation boundary 208 will be addressed. For example, the final estimated projection 206 and the measured projection 202 may not have the same slope at the boundary channel, i=0, even though the magnitude may be the same. To avoid any potential artifacts resulting from such difference, an additional blending process is applied at channels adjacent to the truncation boundary 208 to ensure that the slope is gradually varying.

Figure 9:
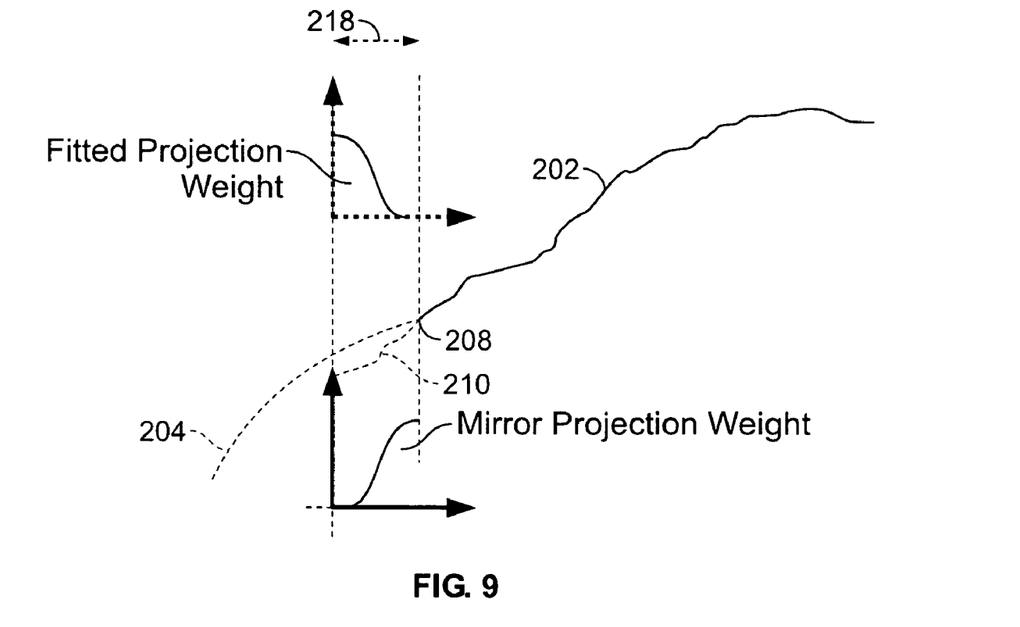
FIG. 9 illustrates the boundary blending process in accordance with an embodiment of the present invention.

FIG. 9 illustrates the boundary blending process in accordance with an embodiment of the present invention. The measured projection 202, fitted projection 204 (FIG. 7), blending region 218 and truncation boundary 208 are indicated. In step 128, the computer 36 generates a small segment of mirror projection 210 ($k_k(i, j)$), that represents a mirror view of the measured projection 202 (non-truncated channels) adjacent the truncation boundary 208 with Equation 15:

$$q_k(i, j) = \begin{cases} 2p_k(0, j) - p_k(-i, j), & q_k(i, j) > 0 \\ 0, & \text{otherwise} \end{cases} \quad -n_b \leq i < 0 \qquad \text{Equation 15}$$

wherein $m_b$ is the number of channels for blending. By way of example, $m_b = 10$.

In step 130, the computer 36 generates a final expanded projection, $\theta_k(i, j)$, at the blending region 218 using a weighted sum of the two estimated projections:

$$\theta_k(i, j) = k_b(j)p''_k(i, j) + (1 - k_d(j))k_k(i, j), \quad -m_k \leq i\,b < 0 \qquad \text{Equation 16}$$

wherein $k_d(i)$ is a monotonically decreasing function from 1 to 0. As the function, $k_k(k,j)$ (Equation 15) ensures the first order continuity of the measured projection at the truncation boundary 208, and the weighting function associated with $k_k(i, j)$ is close to unity at the truncation boundary 208, the resulting function, $\theta_k(i, j)$, should be more or less continuous (first order) to the measured projection 202.

As mentioned previously, the projection estimation process described above is for cases having only left side truncation. This process is also directly applicable to cases having only right side truncation with simple index change, and thus the process for right side truncation will not be repeated. However, in cases wherein both sides of the projection are truncated, the estimated total attenuation, D(k, j), cannot be used directly to guide the estimation of parameters. As D(k, j) represents the total missing truncation from both sides, an estimation process is needed to distribute D(k, j).

The nature of the Sonogram is that any point in the object space is mapped to a sinusoidal curve in the Sonogram space. The characteristics guarantee that the views that are adjacent to the non-truncated view regions have less truncation than the views that are in the middle of the truncation view region. For example, for a truncated projection, a small fraction of D(k, j) is assigned to the left side if the left side is not truncated a few views ago, and vise versa. In addition, if the number of truncated views on the left side associated with the current view is far fewer than the number of truncated views on the right side, the worst amount of truncation on the left side should be much less than the worst truncation on the right side. In step 132, the computer 36 defines the left-right side truncation distribution using Equation 17:

$$\begin{cases} D_L(k, j) = \dfrac{t_L U_L}{t_L U_L + t_R U_R} D(k, j) \\ D_R(k, j) = \dfrac{t_R U_R}{t_L U_L + t_R U_R} D(k, j) \end{cases} \qquad \text{Equation 17}$$

wherein $D_L(k, j)$ and $D_R(k, j)$ are the estimated total missing attenuation for the left and right side of the projection, respectively. $U_L$ and $U_R$ are the number of consecutive views in the current truncation region for the left and right sides, respectively, and $t_L$ and $t_R$ represent the shortest view distance of the current view to the non-truncated views (either preceding or trailing views) for left and right sides. Whenever a large number of views are truncated, it is likely that the amount of truncation on that side is large. If the number of consecutive truncated views is small, it is likely that the edge of the FOV is just grazing the edge of the body, so the amount of missing projection is small. The distribution is proportional to how many consecutive views are on either side.

With the estimated total missing projection truncation for the left and right sides, the truncated projection can be calculated in a similar manner as before. Previously, the scaling factor, g, was calculated in Equation 13. Theoretically, two scaling factors can be calculated for the left and right side. However, the calculation may lead to more errors as the original estimated truncation is further split up into two parts, and the splitting process is also an approximation. Therefore, in step 134, the computer 36 calculates a single scaling factor, g, for both left and right sides with Equation 18:

$$g = \frac{D(k, j)}{\sum_{i=m_k}^{-1} p'_k(i, j) + \sum_{i=N+1}^{N+m'_k} p'_k(i, j)} \quad \text{Equation 18}$$

wherein $m_k$ and $m'_k$ are the extents of truncation for the left and right side, respectively.

As stated previously, truncation detection is based on the readings of the boundary channels. Under many clinical conditions, however, the scanned object may be barely positioned outside the 50 cm FOV. The boundary projection sample values may be just below the truncation detection threshold and thus is not performed.

Therefore, for all non-truncated views identified in step 104, a transition region is established near the measured edge channels. By way of example, the left side is used to describe the process, although it should be noted that the process applies equally to the right side. In step 136, the computer 36 assigns projection readings, $p'_k(i, j)$ in the transition region to the following values using Equation 19:

$$p'_k(i,j) = p_k(0,j) \cdot k_t(j), -m_{ti} \le i \, b < 0 \quad \text{Equation 19}$$

where, $$w_t(i) = 3\left(\frac{i+n_t}{n_t}\right)^2 - 2\left(\frac{i+n_t}{n_t}\right)^3$$

Parameter $m_t$ specifies the length of the transition region. By way of example only, the transition region may be defined as $m_{tab} = 20$. This process guarantees the smooth transition of the measured boundary channels to zero. Note that when the measured boundary channel is actually zero, the Equation 19 has a null effect.

Figure 10:
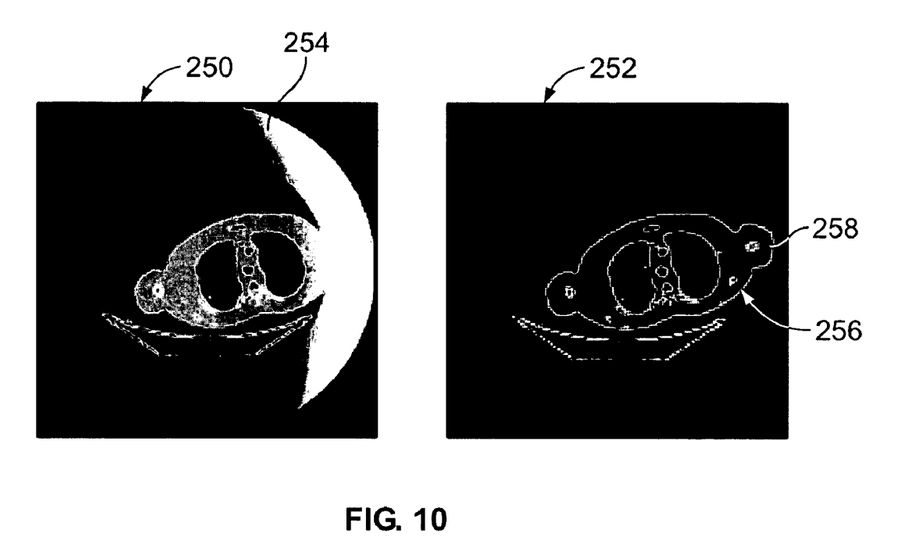
FIG. 10 illustrates a first image without truncation compensation and a second image with truncation compensation in accordance with the present invention.

FIG. 10 illustrates a first image 250 without truncation compensation and a second image 252 with truncation compensation in accordance with the present invention. The first and second images 250 and 252 represent a scanned shoulder phantom positioned near the edge of the gantry opening (70 cm) with a 64×0.625 mm detector configuration at a helical pitch of 63/64:1. A main body portion 256 of the phantom is within the CT detector FOV while an arm portion 258 is outside the CT detector FOV.

Severe truncation artifacts 254 result in the first image 250 for the portions of the phantom outside the detector FOV, which is 50 cm. The second image 252 was reconstructed using the method of FIG. 3. A significant improvement is seen in the reconstructed image outside the 50 cm FOV. As a high density bony structure in the arm deviates significantly from the water material assumption, some streaking or shading artifacts may be present. However, the magnitude of the artifacts does not impact the accuracy of the attenuation correction map.

Figure 11:
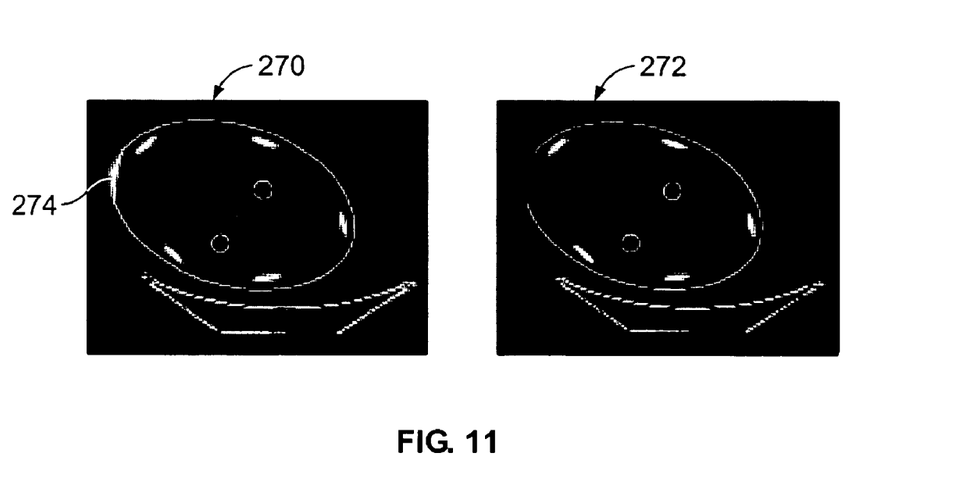
FIG. 11 illustrates first and second images of a helical body phantom with and without transition region correction, respectively, for non-truncated views in accordance with an embodiment of the present invention.

FIG. 11 illustrates first and second images 270 and 272 of a helical body phantom with and without transition region correction, respectively, for non-truncated views in accordance with an embodiment of the present invention. By way of example, the Helical Body phantom may be scanned with a 32×0.625 mm detector configuration at helical pitch of 31/32:1, wherein the phantom extends barely outside the 50 cm FOV.

In the first image 270, because of the discontinuity of the boundary channels with the expanded channel readings (zeroes), bright edge artifacts 274 result. The edge artifacts 274 are not present in the second image 272 when the transition regions within the non-truncated regions are processed as discussed with Equation 19.

A technical effect is providing a method to expand the FOV of a volumetric CT scan. As a result, an increased FOV may be used for volumetric CT scanning and when forming fused images using a CT scan to provide attenuation information for a PET or SPECT scan. A projection profile of the estimated missing projection for truncated views may be calculated based on at least one neighboring non-truncated view.

While the invention has been described in terms of various specific embodiments, those skilled in the art will recognize that the invention can be practiced with modification within the spirit and scope of the claims.

What is claimed is:

1. A method for expanding a field-of-view of a volumetric computed tomography scan, comprising:
   obtaining truncated and non-truncated views of an object using a CT imaging system;
   identifying the truncated views having projection truncation and the non-truncated views without projection truncation based on an average value of one or more edge channels over more than one view;
   calculating an estimated missing projection distribution for each of the truncated views based on at least one neighboring non-truncated view;
   calculating a projection profile for each of the truncated views based on the estimated missing projection distribution, the projection profile providing at least one of attenuation data and projection data for an area outside a field-of-view; and
   displaying an image of the object on a display of the CT imaging system based on the at least one of attenuation data and projection data.

2. The method of claim 1, further comprising:
   identifying a predetermined number of consecutive views adjacent to each of the non-truncated views; and
   reassigning a non-truncated view to be a truncated view when at least one of the consecutive views is a truncated view.

3. The method of claim 1, further comprising:
   calculating a total attenuation curve representative of measured total attenuation for each of the truncated and non-truncated views; and
   identifying a truncation view region between first and second non-truncated views, the truncation view region comprising at least a portion of the truncated views, the estimated missing projection being further based on the truncation view region.

4. The method claim 1, further comprising identifying at least one non-truncated view being closest to a truncated view, the projection profile for the truncated view being further calculated based on a projection profile representative of the at least one non-truncated view.

5. The method claim 1, further comprising:
identifying first and second non-truncated views being closest to a truncated view, the truncated view being located between the first and second non-truncated views;
calculating projection profiles representative of the first and second non-truncated views; and
applying a higher weight to one of the first and second non-truncated views based on a lesser distance from the truncated view, the projection profile for the truncated view being further calculated based on the projection profiles representative of the first and second non-truncated views.

6. The method of claim 1, further comprising:
identifying a truncation boundary between a truncated projection and a measured projection; and
blending the estimated missing projection and a mirror projection based on the measured projection at the truncation boundary to ensure a gradually varying slope adjacent to the truncation boundary.

7. The method of claim 1, further comprising:
identifying the truncated views having both left side and right side truncation; and
distributing the estimated missing projection between the left and right sides based on a scaling factor.

8. The method of claim 1, further comprising:
calculating a location and size of a water cylindrical object based on at least one of a measured projection and an extent of truncation;
calculating an estimated water cylinder projection based on the water cylindrical object; and
deriving a scaling factor for increasing or decreasing the estimated missing projection based on a comparison of the estimated water cylinder projection and the estimated missing projection.

9. A method for expanding a field-of-view of a computed tomography scanner, comprising:
obtaining truncated and non-truncated views of an object using a CT imaging system;
identifying the truncated views having projection truncation and the non-truncated views without projection truncation based on an average value of one or more edge channels over more than one view;
calculating a total estimated missing projection distribution based on a total attenuation curve representative of measured total attenuation for each of the truncated and non-truncated views;
calculating a projection profile for each of the truncated views based on at least one of the total estimated missing projection distribution and a projection profile representative of at least one non-truncated view being closest to each of the truncated views, the projection profile providing at least one of attenuation data and projection data for an area outside a field-of-view; and
displaying an image of the object on a display of the CT imaging system based on the at least one of attenuation data and projection data.

10. The method of claim 9, further comprising:
identifying a transition region near an outer edge of the field-of-view for each non-truncated view;
identifying projection values within the transition region; and
calculating a projection profile extending beyond the field-of-view for each non-truncated view, projection values beyond the field-of-view reducing gradually with respect to the projection values within the transition region.

11. The method of claim 9, further comprising:
identifying a truncation boundary between a truncated projection and a measured projection;
identifying a predetermined number of channels within the measured projection adjacent the boundary region; and
blending the total estimated missing projection near the truncation boundary based on the predetermined number of channels.

12. The method of claim 9, further comprising:
identifying a predetermined number of consecutive views adjacent to each of the non-truncated views; and
reassigning a non-truncated view to be a truncated view when at least one of the consecutive views is a truncated view.

13. The method of claim 9, further comprising increasing or decreasing the total estimated missing projection based on an estimated water cylinder projection of a water cylindrical object, the water cylindrical object being based on at least one of a measured projection and an extent of truncation.

14. The method of claim 9, further comprising:
identifying first and second non-truncated views being closest to a truncated view, the truncated view being located between the first and second non-truncated views; and
calculating an extent of truncation for the truncated view based on the first and second non-truncated views.

15. A system for expanding a field-of-view, comprising:
a computer for receiving computed tomography image data representative of multiple views, the computer configured to:
identify truncated views having projection truncation and non-truncated views without projection truncation based on an average value of one or more edge channels over more than one view;
calculate an estimated missing projection distribution for each of the truncated views based on at least one neighboring non-truncated view; and
calculate a projection profile for each of the truncated views based on the estimated missing projection distribution, the projection profile providing at least one of attenuation data and projection data for an area outside a field-of-view.

16. The system of claim 15, the computer further configured to identify at least one non-truncated view being closest to a truncated view, the projection profile for the truncated view being further calculated based on a projection profile representative of the at least one non-truncated view.

17. The system of claim 15, the computer further configured to:
identify a transition region near an outer edge of the field-of-view for each non-truncated view;
identify projection values within the transition region; and
calculate a projection profile extending beyond the field-of-view for each non-truncated view, projection values beyond the field-of-view reducing gradually with respect to the projection values within the transition region.

18. The system of claim 15, the computer further configured to:
identify first and second non-truncated views being closest to a truncated view, the truncated view being located between the first and second non-truncated views; and calculate an extent of truncation for the truncated view based on the first and second non-truncated views.

19. The system of claim 15, the computer further configured to:
determine shortest view distances for each of left and right sides of a current truncated view to a non-truncated view; and
distribute the estimated missing projection between the left and right sides based on the shortest view distances.

20. The system of claim 15, the computer further configured to:
calculate a location and size of a water cylindrical object based on at least one of a measured projection and an extent of truncation;
calculate an estimated water cylinder projection based on the water cylindrical object; and
derive a scaling factor for increasing or decreasing the estimated missing projection based on a comparison of the estimated water cylinder projection and the estimated missing projection.

* * * * *